(12) United States Patent
Glock

(10) Patent No.: US 9,439,927 B2
(45) Date of Patent: Sep. 13, 2016

(54) TREATMENT OF INFLAMMATORY BOWEL DISEASE

(71) Applicant: Glock Health GmbH, Deutsch Wagram (AT)

(72) Inventor: Gaston Glock, Velden (AT)

(73) Assignee: Glock Health GmbH (AT)

( * ) Notice: Subject to any disclaimer, the term of this patent is extended or adjusted under 35 U.S.C. 154(b) by 0 days.

(21) Appl. No.: 14/537,088

(22) Filed: Nov. 10, 2014

(65) Prior Publication Data

US 2015/0132387 A1 May 14, 2015

(30) Foreign Application Priority Data

Nov. 8, 2013 (EP) .................................... 13192094

(51) Int. Cl.
*A61K 9/14* (2006.01)
*A61K 33/08* (2006.01)
*A61K 33/06* (2006.01)

(52) U.S. Cl.
CPC .............. *A61K 33/08* (2013.01); *A61K 33/06* (2013.01)

(58) Field of Classification Search
None
See application file for complete search history.

(56) References Cited

U.S. PATENT DOCUMENTS

| 6,287,576 B1 * | 9/2001 | Bgatov | .................. | A61K 36/02 424/400 |
| 6,303,572 B1 * | 10/2001 | Rowe | ..................... | A61K 38/12 424/184.1 |
| 2012/0045526 A1 * | 2/2012 | Gast | ....................... | A61K 33/06 424/684 |

OTHER PUBLICATIONS

Z. Adamis et al., "In Vitro and in Vivo Tests for Determination of the Pathogenicity of Quartz, Diatomaceous Earth, Mordenite and Clinoptilolite", Annals of Occupational Hygiene, vol. 44, No. 1, 2000, pp. 67-74.
Y. Alcala-Canto et al., "Effects of clinoptilolite on *Eimeria* spp. infection in sheep", Small Ruminant Research 100; 2-3, 184-188, 2011.
S.E. Bachman et al., "Early aspects of locoweed toxicosis and evaluation of a mineral supplement or clinoptilolite as dietary treatments", Journal of Animal Science, vol. 70, 1992, pp. 3125-3132.
P. Bartko et al., "The effect of feeding zeolite (clinoptilolite) on the health status of sheep", summary, Veterinary Medicine, vol. 28, No. 8, 1983, pp. 481-492.

Mahaboob P. Basha et al., "Neuroprotective Actions of Clinoptilolite and Ethylenediaminetetraacetic Acid Against Lead-Induced Toxicity in Mice Mus musculus", Toxicology International, vol. 20, No. 3, Sep.-Dec. 2013, pp. 201-207.
A. Batista et al., "Adjuvant effect of CliptoxTM on the protective immune response induced by an inactivated vaccine against foot and mouth disease virus in mice", Vaccine, vol. 28, 2010, pp. 6361-6366.
Michaela Beltcheva et al., "Modified Natural Clinoptilolite Detoxifies Small Mammal's Organism Loaded with Lead I. Lead Disposition and Kinetic Model for Lead Bioaccumulation", Biological Trace Element Research, Dec. 7, 2011, 9 pages.
M.C. Bonferoni et al., "ZN2+-exchanged clinoptilolite-rich rock as active carrier for antibiotics in anti-acne topical therapy In-vitro characterization and preliminary formulation studies", Applied Clay Science, vol. 36, 2007, pp. 95-102.
Phillip D. Bowman et al., "Toxicity of Aluminum Silicates Used in Hemostatic Dressings Toward Human Umbilical Veins Endothelial Cells, HeLa Cells, and RAW267.4 Mouse Macrophages", The Journal of Trauma Injury, Infection, and Critical Care, vol. 71, No. 3, Sep. 2011, pp. 727-732.
K.M. Cammack et al., "Effects of high-sulfur water and clinoptilolite on health and growth performance of steers fed forage-based diets", Journal of Animal Science, vol. 88, Jan. 15, 2010, pp. 1777-1785.
K. Deligiannis et al., "The effect of feeding clinoptilolite on food intake and performance of growing lambs infected or not with gastrointestinal nematodes", Livestock Production Science, vol. 96, 2005, pp. 195-203.
Ramazan Demírel et al., "Effects of Dietary Zeolite on Serum Contents and Feeding Performance in Rats", International Journal of Agriculture and Biology, vol. 13, No. 3, 2011, pp. 346-350.
Amy R. Elmore, "Final Report on the Safety Assessment of Aluminum Silicate, Calcium Silicate, Magnesium Aluminum Silicate, Magnesium Silicate, Magnesium Trisilicate, Sodium Magnesium Silicate, Zirconium Silicate, Attapulgite, Bentonite, Fuller's Earth, Hectorite, Kaolin, Lithium Magnesium Silicate, Lithium Magnesium Sodium Silicate, Montmorillonite, Pyrophyllite, and Zeolite", International Journal of Toxicology, vol. 22, Supplement 1, 2003, pp. 37-102.
James L. Flowers et al., "Clinical evidence supporting the use of an activated clinoptilolite suspension as an agent to increase urinary excretion of toxic heavy metals", Nutrition and Dietary Supplements, vol. 1, Nov. 10, 2009, pp. 11-18.
P. Fokas et al., "Assessment of Pb retention coefficient and nutrient utilization in growing pigs fed diets with added clinoptilolite", summary, Animal Feed Science and Technology, Jun. 5, 2004, 2 pages.

(Continued)

*Primary Examiner* — Robert A Wax
*Assistant Examiner* — Quanglong Truong
(74) *Attorney, Agent, or Firm* — Kolisch Hartwell, P.C.

(57) ABSTRACT

The invention relates to the treatment of inflammatory bowel disease, also termed IBD, including ulcerative colitis and Crohn's disease. To this end, the invention proposes clinoptilolite having a particle size between 0.2 and 1 µm for use in the treatment of inflammatory bowel disease, also termed IBD, in mammals and humans. In the case of such use, the clinoptilolite is preferably freed of heavy metals. In one variant, it is administered orally, optionally with pharmaceutically harmless carrier materials and/or diluents.

14 Claims, 6 Drawing Sheets

(56) References Cited

OTHER PUBLICATIONS

Figure 1:
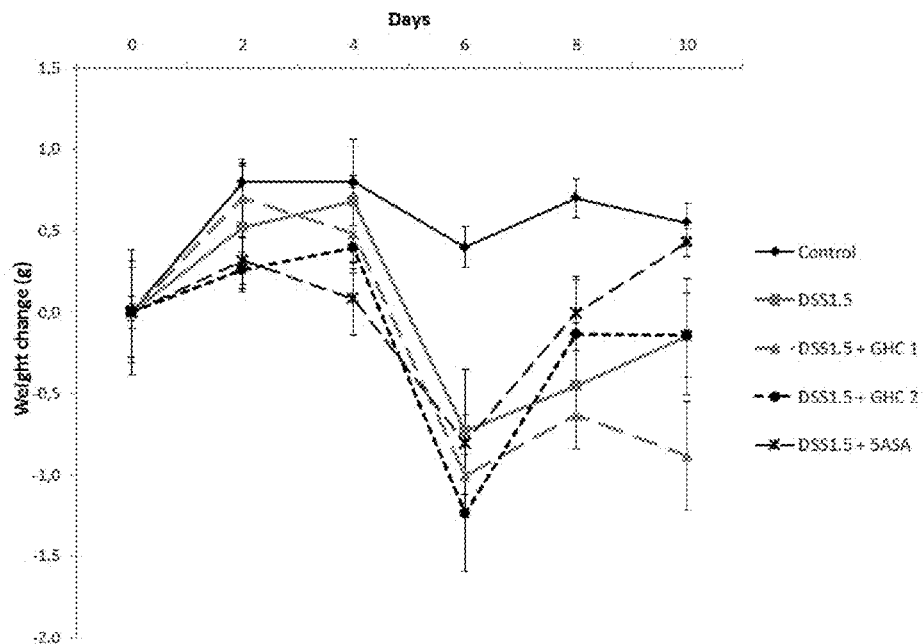

S. Forberg et al., "Can Zeolites Decrease the Uptake and Accelerate the Excretion of Radio-caesium in Ruminants?", The Science of the Total Environment, vol. 79, 1989, pp. 37-41.

M.L. Galyean et al., "Effects of sodium bentonite, buffer salts, cement kiln dust and clinoptilolite on rumen characteristics of beef steers fed a high roughage diet", summary, Journal of Animal Science, vol. 52, No. 5, May 1981, pp. 1197-1204.

I. Herzig et al., "Long-term application of clinoptilolite via the feed of layers and its impact on the chemical composition of long bones of pelvic limb (femur and tibiotarsus) and eggshell", Veterinarni Medicina, vol. 53, No. 10, 2008, pp. 550-554.

Slavko Ivkovic et al., "Dietary Supplementation With the Tribomechanically Activated Zeolite Clinoptilolite in Immunodeficiency: Effects on the Immune System", Advances in Natural Therapy, vol. 21, No. 2, Mar./Apr. 2004, pp. 135-148.

U. Jacobi et al., "The effect of zeolite (clinoptilolite) on the post-feeding dynamics of N metabolism in the portal vein, jugular vein and the rumen fluid of bulls", summary, Veterinary Medicine, vol. 29, No. 4, Apr. 1984, pp. 207-216.

Bock-Gie Jung et al., "Dietary aluminosilicate supplement enhances immune activity in mice and reinforces clearance of porcine circovirus type 2 in experimentally infected pigs", Veterinary Microbiology, vol. 143, 2010, pp. 117-125.

M.A. Karatzia et al., "Effects of in-feed inclusion of clinoptilolite on blood serum concentrations of aluminium and inorganic phosphorus and on ruminal pH and volatile fatty acid concentrations in dairy cows", summary, Biological Trace Element Research, vol. 142, No. 2, Aug. 2011, pp. 159-166.

Masa Katic et al., "A clinoptilolite effect on cell media and the consequent effects on tumor cells in vitro", Frontiers in Bioscience, vol. 11, May 1, 2006, pp. 1722-1732.

P.D. Katsoulos et al., "Effects on blood concentrations of certain serum fat-soluble vitamins of long-term feeding of dairy cows on a diet supplemented with clinoptilolite", summary, Journal of Veterinary Medicine, A, Physiology, Pathology, Clinical Medicine, vol. 52, No. 4, May 2005, pp. 157-161.

P.D. Katsoulos et al., "Effects of long-term feeding dairy cows on a diet supplemented with clinoptilolite on certain serum trace elements", summary, Biological Trace Element Research, vol. 108, No. 1-3, Winter 2005, pp. 137-145.

Panagiotis-Dimitrios Katsoulos et al., "Effects of long-term dietary supplementation with clinoptilolite on incidence of parturient paresis and serum concentrations of total calcium, phosphate, magnesium, potassium, and sodium in dairy cows", American Journal of Veterinary Research, vol. 66, No. 12, Dec. 2005, pp. 2081-2085.

P.D. Katsoulos et al., "Effects of long-term feeding of a diet supplemented with clinoptilolite to dairy cows on the incidence of ketosis, milk yield and liver function", summary, Veterinary Record, vol. 159, No. 13, Sep. 23, 2006, pp. 415-418.

P.D. Katsoulos et al., "Effect of long-term dietary supplementation with clinoptilolite on performance and selected serum biochemical values in dairy goats", summary, American Journal of Veterinary Research, vol. 70, No. 3, Mar. 2009, pp. 346-352.

Elham Khodaverdi et al., "Evaluation of synthetic zeolites as oral delivery vehicle for anti-inflammatory drugs", Iranian Journal of Basic Medical Sciences, vol. 17, No. 5, May 2014, pp. 337-343.

L.G. Korkina et al., "Mechanism of the cytotoxic action of the natural zeolite clinoptilolite", summary, Farmakol Toksikol, vol. 47, No. 5, Sep.-Oct. 1984, pp. 63-67.

Danina Krajišnik et al., "Cationic Surfactants-Modified Natural Zeolites: Potential Excipients for Anti-Inflammatory Drugs", Proceedings of the 3rd Croatian-Slovenian Symposium on Zeolites, 2010, pp. 23-26.

G.G. Kruglikov et al., "The structural-functional changes in pulmonary macrophages during the phagocytosis of a natural zeolite-clinoptilolite", summary, Gigiena Truda I Professionalnye Zabolevaniia, No. 11-12, 1992, pp. 44-46.

S.C. Kyriakis et al., "Experimental studies on safety and efficacy of the dietary use of a clinoptilolite-rich tuff in sows: a review of recent research in Greece," Microporous and Mesoporous Materials, vol. 51, 2002, pp. 65-74.

S. Leung et al., "Zeolite (clinoptilolite) as feed additive to reduce manure mineral content," Bioresource Technology, vol. 98, 2007, pp. 3309-3316.

Zouhir Mallek et al., "Effect of zeolite (clinoptilolite) as feed additive in Tunisian broilers on the total flora, meat texture and the production of omega 3 polyunsaturated fatty acid", Lipids in Health and Disease, vol. 11, No. 35, 2012, 7 pages.

I. Martin-Kleiner et al., "The effect of the zeolite clinoptilolite on serum chemistry and hematopoiesis in mice", Food and Chemical Toxicology, vol. 39, 2001, pp. 717-727.

F.T. McCollum et al., "Effects of Clinoptilolite on Rumen Fermentation, Digestion and Feedlot Performance in Beef Steers Fed High Concentration Diets", Journal of Animal Science, vol. 56, No. 3, 1983, pp. 517-524.

B. Mitrovic et al., "AFCF and clinoptilolite use in reduction of (137)Cs deposition in several days' contaminated broiler chicks", summary, Journal of Environmental Radioactivity, vol. 95, No. 2-3, 2007, pp. 171-177.

Dorotea Mück-Šeler et al., "The effect of natural clinoptilolite on the serotonergic receptors in the brain of mice with mammary carcinoma", Life Sciences, vol. 73, 2003, pp. 2059-2069.

F. Ništiar et al., "Distribúcia Dichlórvosu v Organizme Krýs a Vplyv Klinoptilolitu na Intoxikáciu", Veterinární Medicina, vol. 29, No. LVII, 1984, pp. 689-698.

M.A. Norouzian et al., "The effects of feeding clinoptilolite on hematology, performance, and health of newborn lambs", summary, Biological Trace Element Research, vol. 137, No. 2, Nov. 2010, pp. 168-176.

H. Oğuz et al., "Effects of clinoptilolite on performance of broiler chickens during experimental aflatoxicosis", summary, British Poultry Science, vol. 41, No. 4, Sep. 2000, pp. 512-517.

H. Oğuz et al. "Evaluation of biochemical characters of broiler chickens during dietary aflatoxin (50 and 100 ppb) and clinoptilolite exposure", summary, Research in Veterinary Science, vol. 73, No. 1, Aug. 2002, pp. 101-103.

M.D. Olver, "Effect of feeding clinoptilolite (zeolite) to three strains of laying hens", summary, British Poultry Science, vol. 30, No. 1, Mar. 1989, pp. 115-121.

M. Ortatatli et al., "Evaluation of pathological changes in broilers during chronic aflatoxin (50 and 100 ppb) and clinoptilolite exposure", Research in Veterinary Science, vol. 78, 2005, pp. 61-68.

D.S. Papaioannou et al., "Effect of in-feed inclusion of a natural zeolite (clinoptilolite) on certain vitamin, macro and trace element concentrations in the blood, liver and kidney tissues of sows", Research in Veterinary Science, vol. 72, 2002, pp. 61-68.

D.S. Papaioannou et al., "A field study on the effect of in-feed inclusion of a natural zeolite (clinoptilolite) on health status and performance of sows/gilts and their litters", summary, Research in Veterinary Science, vol. 72, No. 1, Feb. 2002, pp. 51-59.

D.S. Papaioannou et al., "A field study on the effect of the dietary use of a clinoptilolite-rich tuff, alone or in combination with certain antimicrobials, on the health status and performance of weaned, growing and finishing pigs", summary, Research in Veterinary Science, vol. 76, No. 1, Feb. 2004, pp. 19-29.

S.S. Parlat et al., "Effect of clinoptilolite on performance of Japanese quail (Coturnix coturnix japonica) during experimental aflatoxicosis", summary, British Poultry Science, vol. 40, No. 4, Sep. 1999, pp. 495-500.

Krešimir Pavelić et al., "Natural zeolite clinoptilolite: new adjuvant in anticancer therapy", Journal of Molecular Medicine, 2001, 26 pages.

K. Pavelic et al., "Immunostimulatory effect of natural clinoptilolite as a possible mechanism of its antimetastatic ability", Journal of Cancer Research and Clinical Oncology, Nov. 10, 2001, 13 pages.

W.G. Pond et al., "Decreased Absorption of Orally Administered Ammonia by Clinoptilolite in Rats (41076)", Proceedings of the Society for Experimental Biology and Medicine, vol. 166, 1981, pp. 369-373.

(56) References Cited

OTHER PUBLICATIONS

W.G. Pond et al., "Protection by clinoptilolite or zeolite NaA against cadmium-induced anemia in growing swine", summary, Proceedings of the Society for Experimental Biology and Medicine, vol. 173, No. 3, Jul. 1983, pp. 332-337.
W.G. Pond et al., "Reproduction and Progeny Growth in Rats Fed Clinoptilolite in the Presence or Absence of Dietary Cadmium", Bulletin of Environmental Contamination and Toxicology, vol. 31, 1983, pp. 666-672.
W.G. Pond, "Effects of dietary protein level and clinoptilolite on the weight gain and liver mineral response of growing lambs to copper supplementation", summary, Journal of Animal Science, vol. 67, No. 10, Oct. 1989, pp. 2772-2781.
W.G. Pond et al., "Tissue Mineral Element Content in Swine Fed Clinoptilolite", Bulletin of Environmental Contamination and Toxicology, vol. 42, 1989, pp. 735-742.
W.G. Pond et al., "Bone Density and Tissue Lead Accretion in Growing Rats Fed Low High Calcium With or Without Supplemental Clinoptilolite", Bulletin of Environmental Contamination and Toxicology, vol. 57, 1996, pp. 713-721.
Wilna Potgieter et al., "Potentiated clinoptilolite: artificially enhanced aluminosilicate reduces symptoms associated with endoscopically negative gastroesophageal reflux disease and nonsteroidal anti-inflammatory drug induced gastritis", Clinical and Experimental Gastroenterology, vol. 7, 2014, pp. 215-220.
Hanne Damgaard Poulsen et al., "Effects of dietary inclusion of a zeolite (clinoptilolite) on performance and protein metabolism of young growing pigs", Animal Feed Science and Technology, vol. 53, 1995, pp. 297-303.
D. Prvulović et al., "Effects of a clinoptilolite supplement in pig diets on performance and serum parameters", Czech Journal of Animal Science, vol. 52, No. 6, 2007, pp. 159-164.
D. Prvulovic et al., "The Influence of Hydrated Aluminosilicate on Biochemical and Haematological Blood Parameters, Growth Performance and Carcass Traits of Pigs", Journal of Animal and Veterinary Advances, vol. 11, No. 1, 2012, pp. 134-140.
L.N. Pylev et al., "Possible carcinogenic hazard of zeolite-clinoptilolite", summary, Gigiena Truda I Professionalnye Zabolevaniia, vol. 3, Mar. 1984, pp. 48-51.
L. Rizzi et al., "Aflatoxin B1 and Clinoptilolite in Feed for Laying Hens: Effects on Egg Quality, Mycotoxin Residues in Livers, and Hepatic Mixed-Function Oxygenase Activities", Journal of Food Protection, vol. 66, No. 5, 2003, pp. 860-865.
L.P. Romanova et al., Liver regeneration after its mechanical injury in rats receiving biologically active substances "Trepel" and "Suvar", summary, Morfologiia, vol. 140, No. 4, 2011, pp. 38-41.
A.A. Sadeghi et al., "Effects of natural zeolite clinoptilolite on passive immunity and diarrhea in newborn Holstein calves", Livestock Science, vol. 113, 2008, pp. 307-310.
M. Safaeikatouli et al., "An Evaluation on the Effects of Dietary Kaolin and Zeolite on Broilers Blood Parameters, T4, TSH and Growth Hormones", Pakistan Journal of Nutrition, vol. 10, No. 3, 2011, pp. 233-237.
A. Safameher, "Effects of Clinoptilolite on Performance, Biochemical Parameters and Hepatic Lesions in Broiler Chickens During Aflatoxosis", Journal of Animal and Veterinary Advances, vol. 7, No. 4, 2008, pp. 381-388.
Luca Sardi et al., "The effects of clinoptilolite on piglet and heavy pig production", Italian Journal of Animal Science, vol. 1, 2002, pp. 103-111.

K. Saribeyoglu et al., "Effects of clinoptilolite treatment on oxidative stress after partial hepatectomy in rats", summary, Asian Journal of Surgery, vol. 34, No. 4, Oct. 2011, pp. 153-157.
G.C. Shurson et al., "Effects of Zeolite a or Clinoptilolite in Diets of Growing Swine", Journal of Animal Science, vol. 59, No. 6, 1984, pp. 1536-1545.
Šperanda Marcela et al., "Haematological and Biochemical Parameters of Weaned Piglets Fed on Fodder Mixture Contaminated by Zearalenone with Addition of Clinoptilolite", Acta Veterinaria, vol. 56, No. 2-3, 2006, pp. 121-136.
D.L. Step et al., "Clinical observations, biochemical data, and postmortem and histopathologic findings in young dairy calves fed zeolite clinoptilolite binder combined with milk replacer", summary, American Journal of Veterinary Research, vol. 69, No. 12, 2008, pp. 1587-1594.
E. Straková et al., "The long-term administration of a clinoptilolite-supplemented feed to layers and its effect on performance, haematological parameters and metabolic profile", Czech Journal of Animal Science, vol. 53, No. 5, 2008, pp. 212-218.
Z. Tang et al., "Effect of zinc-bearing zeolite clinoptilolite on growth performance, nutrient retention, digestive enzyme activities, and intestinal function of broiler chickens", summary, Biological Trace Element Research, vol. 158, No. 1, Apr. 2014, pp. 51-57.
Erzsébet Tátrai et al., "Study on Carcinogenicity of Clinoptilolite Type Zeolite in Wistar Rats", Polish Journal Occupational Medicine and Environmental Health, vol. 6, No. 1, 1993 pp. 27-34.
M. Topashka-Ancheva et al., "Modified natural clinoptilolite detoxifies small mammal's organism loaded with lead II: genetic, cell, and physiological effects", summary, Biological Trace Element Research, vol. 147, No. 1-3, Jun. 2012, pp. 206-216.
Vincent H. Varel et al., "Effect of Dietary Copper Sulfate, Aureo SP250, or Clinoptilolite on Ureolytic Bacteria Found in the Pig Large Intestine", Applied and Environmental Microbiology, vol. 53, No. 9, Sep. 1987, pp. 2009-2012.
L. Vrzgula et al., "Effect of Feeding Clonoptilolite on Health Status, Blood Count, and Weight Gains of Pigs", 1982, 4 pages.
L.C. Wang et al., "Protective effects of zinc-bearing clinoptilolite on broilers challenged with *Salmonella pullorum*", Poultry Science, vol. 91, 2012, pp. 1838-1845.
Qui Jue Wu et al., "The effects of natural and modified clinoptilolite on intestinal barrier function and immune response to LPS in broiler chickens", Veterinary Immunology and Immunopathology, vol. 153, 2013, pp. 70-76.
Q.J. Wu et al., "Intestinal Development and Function of Broiler Chickens on Diets Supplemented with Clinoptilolite", Asian Australasian Journal of Animal Science, vol. 26, No. 7, Jul. 2013, pp. 987-994.
Q.J. Wu et al., "Effects of clinoptilolite and modified clinoptilolite on the growth performance, intestinal microflora, and gut parameters of broilers", Poultry Science, vol. 92, 2013, pp. 684-692.
Yanan Wu et al., "Effects of Clinoptilolite on Growth Performance and Antioxidant Status in Broilers", Biological Trace Element Research, vol. 155, 2013, pp. 228-235.
Simona Zarcula et al., "Clinical Observations in Calves Fed Colostrum Supplemented with Clinoptilolite", Lucrări Ştiintifice Medicină Veterinară, vol. XLII, No. 2, 2010, pp. 64-69.
N. Zarkovic et al., "Anticancer and antioxidative effects of micronized zeolite clinoptilolite", summary, Anticancer Research, vol. 23, No. 2B, Mar.-Apr. 2003, pp. 1589-1595.

* cited by examiner

TREATMENT OF INFLAMMATORY BOWEL DISEASE

The invention relates to the treatment of inflammatory bowel disease, also termed IBD, including ulcerative colitis and Crohn's disease, in accordance with the preamble of Claim 1.

WO 2010/061355 discloses administering clinoptilolite orally "for treating various medical conditions in humans". In such treatment, a specially pretreated clinoptilolite, termed "potentiated clinoptilolite", is used. The conditions to be treated that are mentioned in the description also include IBS, short for "irritable bowel syndrome", a condition which is completely different from IBD:

IBS is a diagnosis of exclusion, which is not made directly by targeted examinations, but instead comes about indirectly by systematic exclusion of other condition causes. It is so to speak a negative intersection of all possible diagnoses; it is an "insignificant", prognostically benign condition of high prevalence, which is neither life-threatening nor life-shortening.

However, IBD relates to two serious symptoms, Crohn's disease and ulcerative colitis, which can be potentially lethal if untreated and, even with adequate treatment, lower life expectancy. Diagnosis generally entails rectosigmoidoscopy, colonoscopy and/or gastroscopy and is often underpinned by histological investigations.

The clinical study presented in the WO document for IBS (in which the presence of IBD was explicitly ruled out by rectosigmoidoscopy) does not in any way predict or give any expectation of efficacy in the case of IBD, simply because medically completely different symptoms are concerned, which are also treated completely differently in the prior art:

IBS using linaclotide,

IBD using ASA, local glucocorticoids such as budenoside, monoclonal antibodies (for example against TNF such as adamalimumab and infliximab or against $\alpha_4\beta_7$ integrin such as vedolizumab).

As stated, customary treatments of IBD occur using derivatives of 5-aminosalicylic acid, using systemically or locally administered glucocorticoids and using immunosuppressants such as azathioprine. However, these medicaments lead to a number of severe, unpleasant side effects, and so they can only be used to a limited extent.

There is therefore a need for a substance or agent, or a medicament, or a cure, which effectively controls such conditions without, or at least with reduced, stress on the patient as a result of side effects.

It is an object of the invention to specify such a medicament or agent or such a cure or treatment.

This is achieved by the features specified in the characterizing part of Claim 1. In other words, inflammatory bowel disease, also termed IBD, is treated by administering, preferably orally, a clinoptilolite which, preferably, is freed of heavy metals, for example by the method of the applicant as per EP 2 040 837, corresponding to U.S. Pat. No. 8,173,101, and which has a particle size between 0.2 and 1 μm. For jurisdictions in which this is possible or required, the invention consists in using clinoptilolite which is preferably freed of heavy metals and which has a particle size between 0.2 and 1 μm in order to produce a medicament for treating the condition(s) mentioned at the beginning.

Clinoptilolite is the collective name for a group of minerals from the group of the zeolites within the "tectosilicates" mineral class. The mineral group crystallizes monoclinically and is, in the form of a solid solution series, composed of all variations of the following idealized end members:

Clinoptilolite-Ca: $Ca_3(Si_{30}Al_6)O_{72}.20H_2O$
Clinoptilolite-K: $K_6(Si_{30}Al_6)O_{72}.20H_2O$
Clinoptilolite-Na: $Na_6(Si_{30}Al_6)O_{72}.20H_2O$ Chemically, they are thus "water-containing" aluminosilicates having the cations calcium, potassium or sodium incorporated in the crystal lattice.

Because of their monoclinic nature, clinoptilolites usually develop tabular crystals, but they also occur in the form of bulky mineral aggregates. In pure form, clinoptilolite crystals are colorless and transparent. However, they can also appear white as a result of multiple light refraction owing to lattice defects or polycrystalline formation or assume a yellowish-white to reddish-white color as a result of foreign inclusions, the transparency decreasing accordingly.

Clinoptilolites, which are present in large (or workable) amounts are usually minerals of sedimentary origin and arise from deposits of volcanic origin such as tuffs and volcanic glasses. In addition, clinoptilolite may also be present in cavities of other igneous rocks such as andesite, basalt or rhyolite. Accompanying minerals of clinoptilolite are further zeolites, halite, quartz, calcite, opal, montmorillonite, hectorite, gaylussite, thenardite and celadonite. Economically profitable deposits can be found in, for example, Cornwall/England; Vogelsberg, Franconia/Germany; Styria/Austria; Andalusia/Spain; Ionian Islands/Greece; east coast of Turkey; Honshu/Japan; southern New Zealand; Chubut/Argentina; South Dakota, Wyoming and also the west coast of the USA and Nova Scotia, Quebec, British Columbia/Canada.

The fact that clinoptilolite is used in pharmaceutical applications is disclosed not only by the printed publication cited at the beginning (see Colella, C: A critical reconsideration of biomedical and veterinary applications of natural zeolites (2011). Clay Minerals 46: 295-309).

Figure 2:
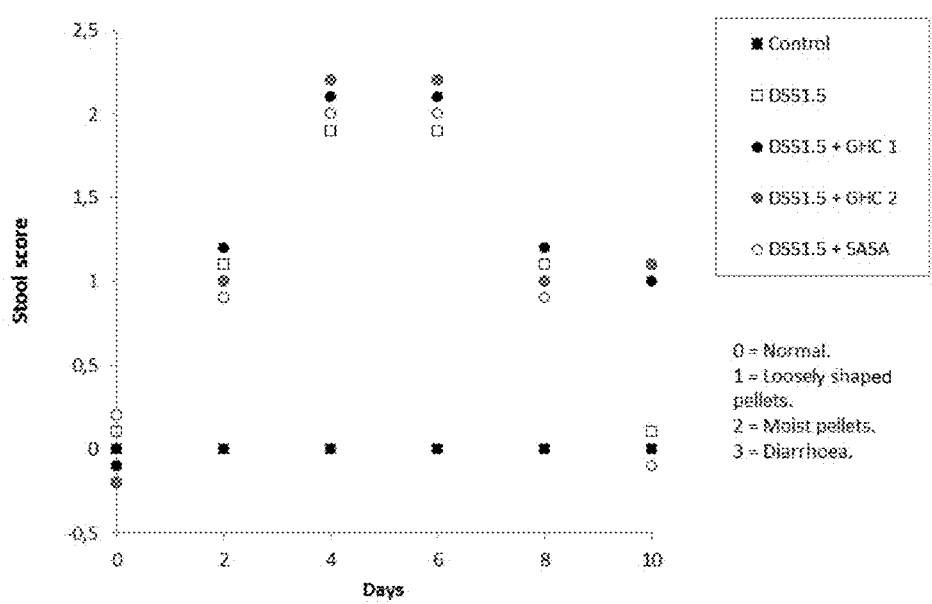
Figure 3:
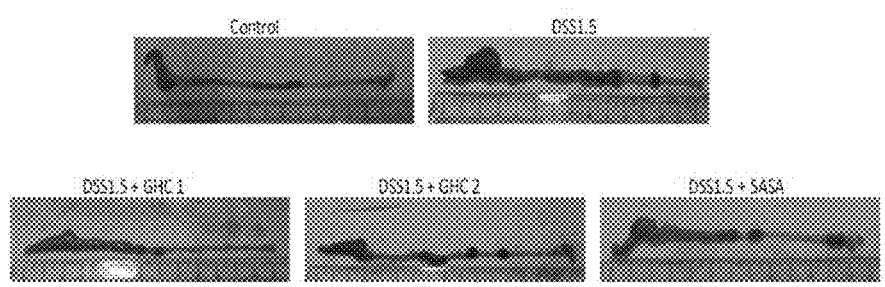
Figure 4:
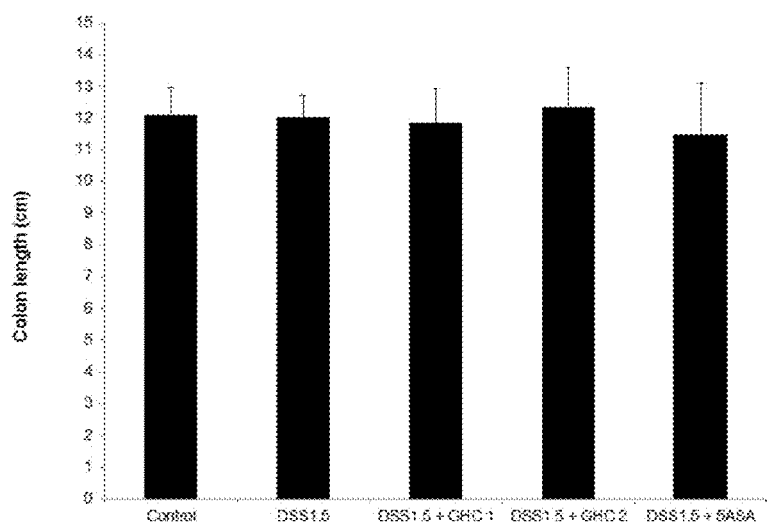
Figure 5:
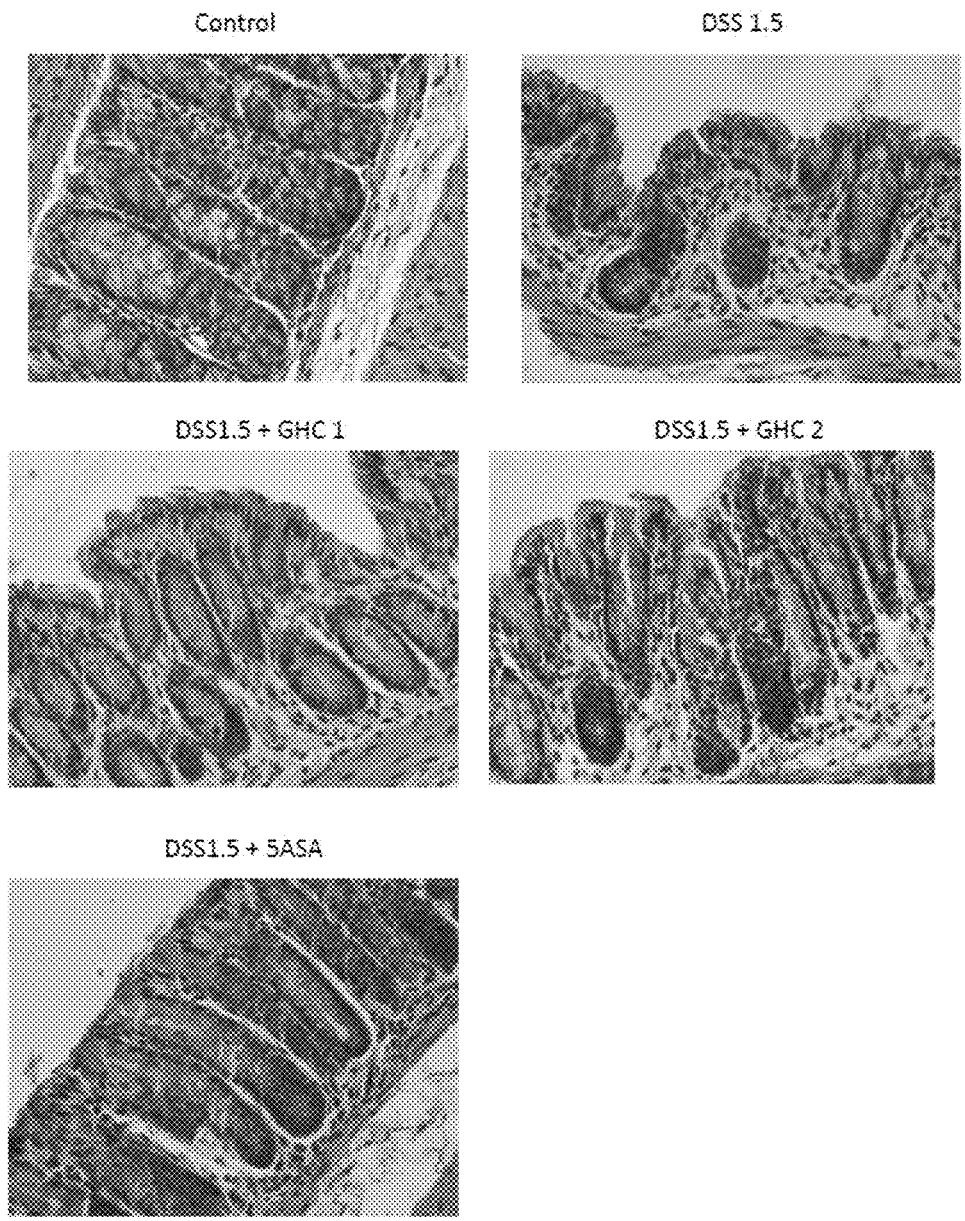
Figure 6:
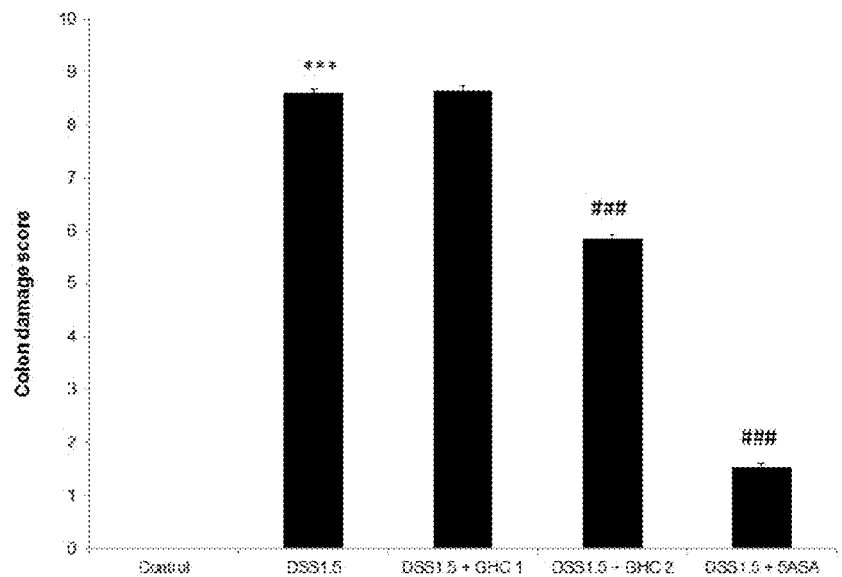
Figure 7:
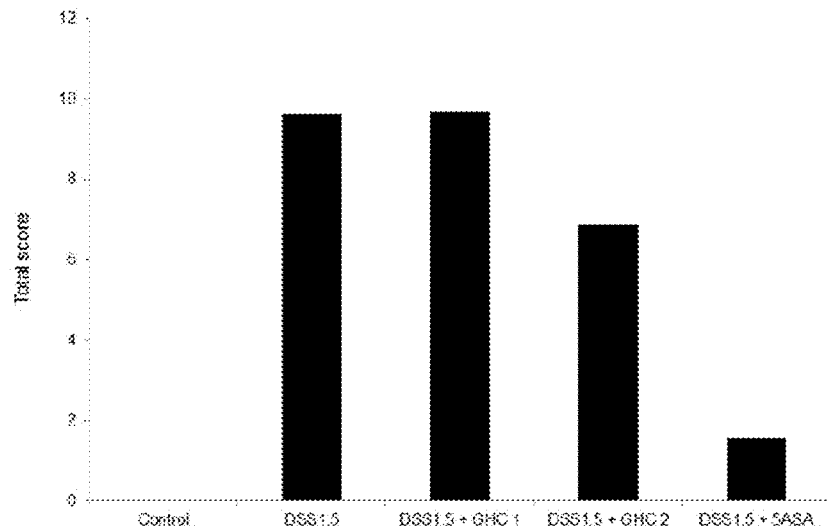

The invention will now be more particularly elucidated with reference to the drawings. In this connection, FIG. 1 shows the change in body weight over days 0-10, FIG. 2 shows the stool consistency over days 0-10, FIGS. 3 and 4 show the colon length of the individual groups, FIG. 5 shows histological images, FIG. 6 shows the damage to the colon, FIG. 7 shows the overall damage, FIGS. 8 to 10 each show the result of various molecular biology analyses and FIG. 11 shows the MPO activity.

The efficacy and the harmlessness of the substance according to the invention are revealed by the analyses and experiments outlined below.

For five groups of 12 mice each (only 3 mice in the control), the experimental routine procedure frequently used in connection with the treatment of IBD was carried out, in which IBD is induced by administration of dextran sulfate sodium (DSS). This involved administering DSS in drinking water for five days (but not in the control group), and after that the particular test substance was administered orally. On the tenth day, the mice were sacrificed using $CO_2$ and the colon was removed for examination. The individual groups were as follows:

Group 1: Control group, did not receive any DSS, only 3 mice, in contrast to 12 mice in each of the other groups.

Group 2: received only DSS.

Group 3: (GHC1) received DSS as described above and, from the sixth day, a clinoptilolite freed of heavy metals which was ground to a mean particle size of 3.5 µm and thus not in accordance with the invention.

Group 4: (GHC2) received, from the sixth day, the substance according to the invention.

Group 5: (5ASA) received, from the sixth day, sulfasalazine, a derivative of mesalazine, also termed 5-ASA.

In summary, the results are as follows: The body weight profile can be seen in FIG. 1. Said figure shows:
  Days;
  Weight change (g);
  Control=control group;
  DSS1.5=group 2;
  DSS1.5+GHC1=group 3;
  DSS1.5+GHC2=(inventive) group 4;
  DSS1.5+5ASA=group 5.

The profile clearly shows that the non-DSS-treated control group, especially on the sixth day, exhibited a distinctly greater weight than all the DSS-treated groups.

What is striking is that the treatment with noninventive clinoptilolite (GHC 1, group 3) appears to hinder rather than support the weight gain following administration in the healing phase, whereas this is not the case for the substance according to the invention (GHC 2, group 3). The substance according to the invention performs only slightly worse than the control group with 5-ASA.

A further feature concerning the efficacy of the administered agent is stool consistency, shown in FIG. 2. Said figure shows:
  Stool score=stool consistency;
  Days;
  Loosely shaped pellets;
  Moist pellets;
  Control=control group;
  DSS1.5=group 2;
  DSS1.5+GHC1=group 3;
  DSS1.5+GHC2=(inventive) group 4;
  DSS1.5+5ASA=group 5.

In line with expectations, there was no change in the control group; the groups treated with clinoptilolite (regardless of particle size) and with 5-ASA were completely within the normal range again on the tenth day. Stool consistency is altered by the substance properties of the two test substances (fine powder) in such a way that the score is not 0 but about 1 even after 10 days. However, the profile clearly shows that stool consistency distinctly improves from day 6 (score >2.0) to day 10 (score 1.0). The substance according to the invention can bind water and the result may therefore be that the feces become altogether softer. However, a value of 1 shows a relatively small change; therefore, a persistence of clinical symptoms cannot really be stated.

The presence of blood in stool is reported in Table I below. Said table shows:
  Blood in stool;
  Mice group;
  Days;
  Control=control group;
  DSS1.5=group 2;
  DSS1.5+GHC1=group 3;
  DSS1.5+GHC2=(inventive) group 4;
  DSS1.5+5ASA=group 5.

As can be seen, blood in stool was detectable (+) from the sixth to the tenth day only in the DSS-treated group. Blood in stool was exhibited by the two clinoptilolite-treated groups (3 and 4) from the sixth to the eighth day and by the 5-ASA-treated group only on the sixth day.

TABLE I

Blood in stool

| Mice group | Days | | | | | |
|---|---|---|---|---|---|---|
|  | 0 | 2 | 4 | 6 | 8 | 10 |
| Control | − | − | − | − | − | − |
| DSS 1.5 | − | − | − | + | + | + |
| DSS 1.5 + GHC 1 | − | − | − | + | + | − |
| DSS 1.5 + GHC 2 | − | − | − | + | + | − |
| DSS + 5ASA | − | − | − | + | − | − |

+ Blood in stool
− No blood in stool

The changes in colon length determined after sacrificing of the animals can be seen qualitatively in the five images of FIG. 3. The figures do not show any distinctive differences between the individual groups. A quantitative evaluation of colon length of the individual groups is shown in FIG. 4 (averaged in each case). Both figures show:
  Control=control group;
  Colon length (cm);
  DSS1.5=group 2;
  DSS1.5+GHC1=group 3;
  DSS1.5+GHC2=(inventive) group 4;
  DSS1.5+5ASA=group 5.

Increasing shortening of the intestine indicates the increasing degree of inflammation. A (statistically insignificant) trend of the substance according to the invention, with respect to all the other groups, of promoting a longer colon can be identified in FIG. 4.

FIG. 5 shows a histological analysis, viz. a representative image of hematoxylin and eosin staining for each test group. Said figure shows:
  Control=control group;
  DSS1.5=group 2;
  DSS1.5+GHC1=group 3;
  DSS1.5+GHC2=(inventive) group 4;
  DSS1.5+5ASA=group 5.

The images show an undamaged intestinal epithelium for the control group (group 1). In contrast, a widespread inflammation can be seen for group 2 (negative control with DSS). Through the treatment with clinoptilolite (regardless of particle size), it was possible to partially speed up the healing of the intestinal epithelium (groups 3 and 4). The positive control group (group 5) shows a distinctly improved healing of the intestinal epithelium with only sparse signs of epithelial damage and immune cell infiltration.

FIG. 6 shows the colon damage score, a determination of intestinal damage on the basis of histo(patho)logical examinations. The colon damage score is derived from (a) destruction of the epithelium (scale from 0 to 3) (b) extension of crypts (scale from 0 to 3) (c) absence of goblet cells (scale from 0 to 3) (d) infiltration of immune cells (scale from 0 to 3) (e) spreading of inflammatory cells (scale from 0 to 3); said figure shows:
  Control=control group;
  DSS1.5=group 2;
  DSS1.5+GHC1=group 3;
  DSS1.5+GHC2=(inventive) group 4;
  DSS1.5+5ASA=group 5;
  Colon damage score=determination of intestinal damage on the basis of histo(patho)logical examinations;
  ***=an extremely significant difference in relation to the control group (control);
  ###=an extremely significant difference in relation to the DDS1.5 group (group 2).

Again, the good convergence of the 5-ASA mice (group 5) and the mice treated with GHC2 according to the invention (group 4) toward the control group can be seen. By contrast, the group which was treated with normal clinoptilolite (GHC1, group 3) cannot be distinguished statistically from the group with no treatment (DSS 1.5, group 1).

FIG. 7 shows the total score, which represents a measure of the overall inflammatory state of the animals. The total score (also termed disease activity index, see Cooper H S, Murthy S N, Shah R S, Sedergran D J. "Clinicopathologic study of dextran sulfate sodium experimental murine colitis". Lab Invest 1993; 69: 238-249.) is derived from the results in FIGS. 2 to 5 and from the content of Table I. The scale in FIG. 6 is accordingly relative and does not have a fixed unit. Said figure shows:

Total score=the overall inflammatory state;
Control=control group;
DSS1.5=group 2;
DSS1.5+GHC1=group 3;
DSS1.5+GHC2=(inventive) group 4;
DSS1.5+5ASA=group 5.

It can be seen from this figure, which displays increasing damage with increasing value (from 0 to 12), that, apart from the control group with 5-ASA, the smallest changes (subsumed in total score=sum of the parameters stool, colon length and intestinal damage score) compared to the control group with no intestinal damage (control) were only to be found in group 4, which received the substance according to the invention. Group 3, which received normal clinoptilolite, does not show any such improvement compared to the group with no treatment (DSS 1.5).

Figure 8:
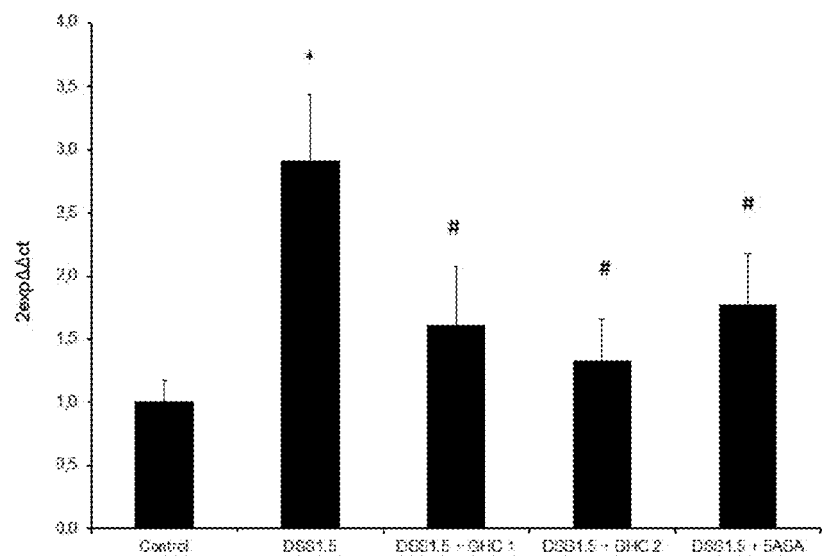

To objectify and quantify the effects determined from the histological examinations, further analyses of biochemical inflammation markers (TNF-α/IL-6/IL-1β mRNA by means of RT-PCR, MPO activity) from tissue homogenates of the relevant intestinal segments were carried out. The results for IL-1β are shown in FIG. 8. Said figure shows:

2expΔΔct=the rise in expression for a particular gene (1=1×, 2=2×, etc.);
Control=control group;
DSS1.5=group 2;
DSS1.5+GHC1=group 3;
DSS1.5+GHC2=(inventive) group 4;
DSS1.5+5ASA=group 5;
*=a significant difference with respect to the control group (control);
=a significant difference with respect to the DDS1.5 group (group 2).

The novel synthesis of IL-1β is shown in FIG. 8. IL-1β is a proinflammatory cytokine, the lowering of which indicates an anti-inflammatory action. Again, better action is detectable in the test group with administration of the substance according to the invention (GHC 2) than in treatment with normal clinoptilolite (GHC 1).

Figure 9:
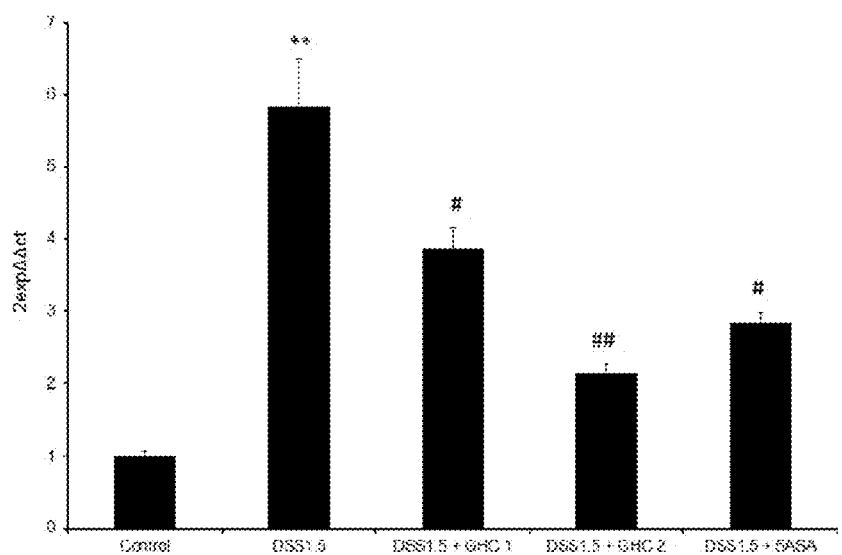

Two further proinflammatory cytokines were examined; the results are shown in FIG. 9 (IL-6) and 10 (TNF-α). Said figures show:

2expΔΔct=the rise in expression for a particular gene (1=1×, 2=2×, etc.);
Control=control group;
DSS1.5=group 2;
DSS1.5+GHC1=group 3;
DSS1.5+GHC2=(inventive) group 4;
DSS1.5+5ASA=group 5;
**=a very significant difference in relation to the control group (control);
=a significant difference in relation to the DDS1.5 group (group 2);
=a very significant difference in relation to the DDS1.5 group (group 2).

In the case of Il-6 (FIG. 9), again only the substance according to the invention (group 4) shows a stronger action than the treatment with normal clinoptilolite (GHC 1); the former is even better than the control with the standard treatment using 5-ASA.

Figure 10:
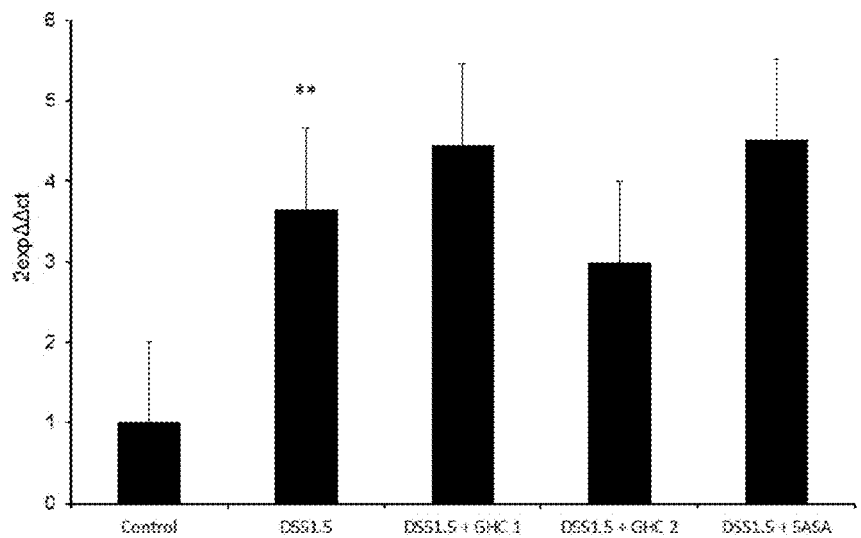
Figure 11:
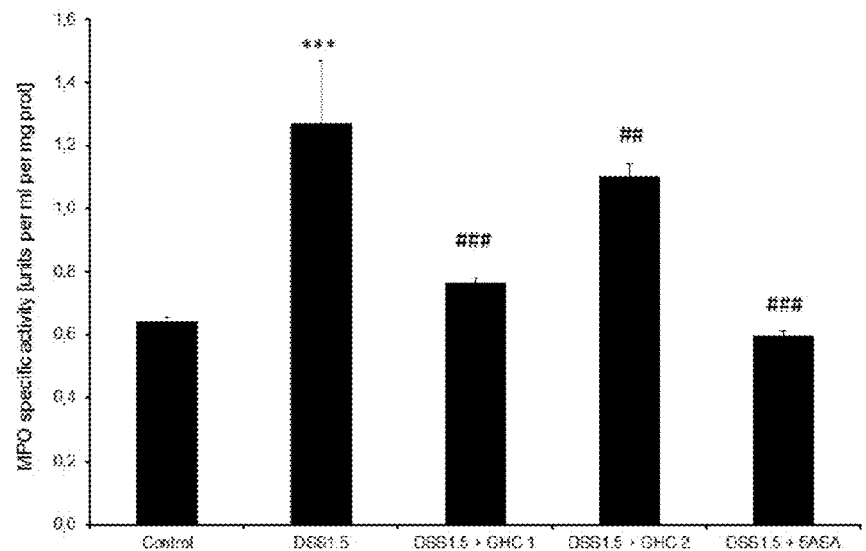

FIG. 10 shows the results for TNF-α; in this case, no statistically significant difference between the substance according to the invention and the control with no treatment (+) is detectable. Since the treatment with 5-ASA also does not show a positive effect on TNF-α, the validity of this parameter for assessing the progress of healing must be cast into doubt.

Lastly, measurements were also further made of the MPO activity in intestinal tissue; the results are shown in FIG. 11. Said figure shows:

Control=control group;
DSS1.5=group 2;
DSS1.5+GHC1=group 3;
DSS1.5+GHC2=(inventive) group 4;
DSS1.5+5ASA=group 5;
MPO specific activity [units per ml per mg prot]=specific MPO activity [units per ml, normalized to protein content];
***=an extremely significant difference in relation to the control group (control);
=a very significant difference in relation to the DDS1.5 group (group 2);
=an extremely significant difference in relation to the DDS1.5 group (group 2).

MPO activity is a customary measurement in IBD studies (Kim J J, Shajib M S, Manocha M M, Khan W I. "Investigating intestinal inflammation in DSS-induced model of IBD" J V is Exp. 2012 Feb. 1; (60)); it represents the inflammation of the intestine through the quantification of the myeloperoxidase produced by infiltrated neutrophils. The results (FIG. 11) show an action of the substance according to the invention and also of the treatment with normal clinoptilolite (group 3). Clearly, the influence on this parameter is based on a different mechanism of action which the action of the substance according to the invention cannot reproduce correspondingly.

The experiments also show that clinoptilolite, both in the particle size of group 3 and in the finely divided sizes according to the invention (group 4), are well tolerated in the animals and the administration thereof does not cause any problems. There were no cases of death caused by the administration of the two test substances or other signs of toxicity.

The clinoptilolite according to the invention is preferably administered orally, on its own or with carrier substances or fillers that are customary in medicine (lactose, glucose, sucrose, starch, calcium sulfate or microcrystalline cellulose).

"Clinoptilolite having a particle size between 0.2 and 1 μm" is understood to mean that clinoptilolite of said particle size is present in an effective amount. Clinoptilolite having a smaller particle size, which is unavoidably included or present owing to the grinding process and despite careful sieving, as well as clinoptilolite having a larger particle size, if present, is not counted or considered. The clinoptilolite which is usable or used according to the invention is obtained by grinding and sieving. The source of the clinoptilolite does not play an appreciable role.

The fact that the particle size of the clinoptilolite has a distinct influence on its efficacy can be clearly seen from the comparison of the results of group 3 (not according to the invention) with the results of group 4 (according to the invention). The particle size distribution within the limits does not have a significant influence on the efficacy.

Said particle size is determined, for example, by sedimentation or by evaluation of the scattering of laser light, or by digital image processing, as is sufficiently known in the prior art.

The duration of administration is individually adapted to the patient by the attending physician according to the course of remission. The same also applies to the dose to be administered, which varies within the range between 1 to 500 mg/kg, preferably between 5 and 100 mg/kg of body weight.

In the case of oral administration, the clinoptilolite according to the invention is optionally admixed with pharmaceutically harmless carrier materials and/or diluents. These are for example: lactose, glucose, sucrose, starch, calcium sulfate, microcrystalline cellulose and many other substances known and used in the prior art.

General Mathematical Remarks Relating to the Assessment:

Significance in analytical statistics is understood to mean the probability that a feature or a characteristic of a random sample is in agreement with the entire population. Said probability is calculated by means of the p-value. The p-value indicates in what percentage % of all cases the actual final result of the entire population will be beyond the calculated range. Depending on the result of the p-value, these can be additionally classified and interpreted:

"Extremely significant" $p \leq 0.001$ less than 0.1% of all cases of the actual overall result are beyond the considered range.

"Very significant" $p \leq 0.01$ less than 1% of all cases of the actual overall result are beyond the considered range.

"Significant" $p \leq 0.05$ less than 5% of all cases of the actual overall result are beyond the considered range.

The invention claimed is:

1. A method of treating inflammatory bowel disease in a mammal, comprising administering to the mammal a therapeutically effective amount of a pharmaceutically acceptable composition of clinoptilolite having a particle size of between 0.2 and 1 µm.

2. The method of claim 1, wherein administering the composition of clinoptilolite includes administering the composition of clinoptilolite orally.

3. The method of claim 1, wherein administering the composition of clinoptilolite includes administering the composition of clinoptilolite to a human.

4. The method of claim 1, wherein the composition of clinoptilolite administered to the mammal includes one or more pharmaceutically acceptable carrier materials.

5. The method of claim 1, wherein the composition of clinoptilolite administered to the mammal includes one or more pharmaceutically acceptable diluents.

6. The method of claim 1, wherein administering the therapeutically effective amount of the composition of clinoptilolite includes orally administering a dose of the composition within a range of between 1 to 500 mg per kg of body weight of the mammal.

7. The method of claim 1, wherein administering the therapeutically effective amount of the composition of clinoptilolite includes orally administering a dose of the composition within a range of between 5 to 100 mg per kg of body weight of the mammal.

8. The method of claim 1, wherein the composition of clinoptilolite administered to the mammal is substantially free of heavy metals.

9. A pharmaceutically acceptable composition of clinoptilolite comprising particles sized between 0.2 and 1 µm that is effective in the treatment of inflammatory bowel disease in mammals.

10. The composition of claim 9, wherein the composition is substantially free of heavy metals.

11. The composition of claim 9, further comprising one or more pharmaceutically acceptable carriers or pharmaceutically acceptable diluents.

12. A pharmaceutically acceptable composition of clinoptilolite consisting essentially of clinoptilolite particles between 0.2 and 1 µm in size.

13. The composition of claim 9, further comprising one or more pharmaceutically acceptable carrier materials.

14. The composition of claim 9, further comprising one or more pharmaceutically acceptable diluents.

* * * * *